US00PP07873P

United States Patent [19]

Klemm

[11] Patent Number: Plant 7,873

[45] Date of Patent: May 26, 1992

[54] GERANIUM PLANT NAMED KLESEC

[75] Inventor: Siegfried Klemm, Stuttgart, Fed. Rep. of Germany

[73] Assignee: Klemm & Sohn, Fed. Rep. of Germany

[21] Appl. No.: 513,942

[22] Filed: Apr. 24, 1990

[51] Int. Cl.[5] ..... A01H 5/00
[52] U.S. Cl. ..... Plt./68
[58] Field of Search ..... Plt./68

[56] References Cited

U.S. PATENT DOCUMENTS

P.P. 7,080 12/1989 Hofmann ..... Plt. 68

*Primary Examiner*—Howard J. Locker
*Attorney, Agent, or Firm*—Charles W. Rummler

[57] ABSTRACT

A new and distinctive Geranium variety particularly distinguished by its vigorous growth habit and its profuse production of brilliant red colored florets which form large long lasting umbel shaped clusters. The individual flowers are comprised of 7 to 8 petals, all of the same brilliant red color. The cluster stalks stand upright holding the flower clusters well above the dark green zonated leaves.

1 Drawing Sheet

BACKGROUND OF THE PLANT

My new Geranium cultivar originated as a hybrid seedling produced by my crossing the variety 'Isabell' U.S. Plant Pat. No. 7,080 with the pollen of the variety 'Alex' U.S. Plant Pat. No. 5,311 in 1984 in my nursery at Stuttgart, West Germany. This seedling bloomed for the first time in 1987 and because of its outstanding growth habit, its profuse blooms, and flower color this seedling was selected for propagation which was done by me and under my direction at Stuttgart by means of cuttings. Successive generations of this plant by cuttings have shown that its novel and distinguishing characteristics are fixed and hold true from generation to generation.

DESCRIPTION OF THE DRAWING

This new Geranium cultivar is illustrated by the accompanying photographic drawing, which shows a fully developed plant with several clusters of flowers and buds which illustrate their form and their brilliant red coloring; the color rendition being as nearly true to that herein specified as is reasonably possible to obtain by conventional photographic procedures.

DESCRIPTION OF THE PLANT

The following is a detailed description of my new geranium plant as observed of plants grown both in greenhouses and outdoors at Stuttgart, with the color designation being according to The R.H.S. Colour Chart published by The Royal Horticultural Society of London, England.

THE PLANT

Origin: Seedling.
Parentage:
*Seed parent.*—Isabell U.S. Plant Pat. No. 7,080.
*Pollen Parent.*—Alex U.S. Pat. No. 5,311.
Classification:
*Botanic.*—*Pelargonium* × *hortorum* Bailey.
*Commercial.*—Zonal Geranium.
Form: Compact, upright bush.

Height: About 24 cm. from the media surface without flower clusters.
Growing rate: Medium.
Branching character: Free basal branching.
Growth habit: Upright.
*Strength.*—Medium. Stands upright without artificial support.
Foliage:
*Quantity.*—Average.
*Shape of leaf.*—Open and half-round. With bicrenate margins.
Size.—About 7-8 cm. wide.
*Texture.*—Smooth.
*Color.*—Upper-side — dark green 147-A with zone of 136-A. Under side — green 137-B.
Veination: Palmate.
Petioles:
*Length.*—About 6 cm.

THE BUD

Size: Medium.
*Diameter.*—About 9 mm.
*Length.*—About 14 mm.
Shape: Ovoid and pointed.
Opening rate: Medium to slow.
Color of petals:
*When sepals first divide.*—44-B.
*When petals begin to unfurl.*—40-A.
Sepals:
*Number.*—5.
*Shape.*—Small and pointed.
*Character.*—The sepals stand up when the flowers open.
*Color.*—Green.
Calyx:
*Shape.*—Broad — Cup-shaped.
*Aspect.*—Smooth.
*Splitting.*—Calyx does not split.
Peduncle: About 14 to 18 cm. long.
*Color.*—Green 137-B.

INFLORESCENCE

Blooming habit: Profuse and continuous from early Spring through Fall until frost.

Size of cluster: Medium.

*Diameter.*—In average about 12 cm.

*Depth.*—In average about 7 cm.

*Borne.*—On an upright stalk.

Cluster stem:

*Length.*—About 14 to 18 cm.

*Color.*—Green with a little brown 137-B.

Florets:

*Diameter.*—About 4.5 cm.

*Depth.*—About 8 mm.

*Shape.*—When blossom first opens — cup shaped. When bloom matures — cup shaped, but filled with petals and petaloids.

*Number.*—About 40 per cluster.

*Form.*—Flattened cup-shaped.

Petalage:

*Number.*—About 7 or 8.

*Form.*—Reniform — with entire margins.

*Arrangement.*—Imbricated.

*Persistence.*—6 to 8 days on stem.

*Texture.*—Soft.

*Appearance.*—Satiny.

*Color.*—All petals — Body — 40A. Base — 44B. Reverse side — 41B. The color remains the same through all seasons.

Lasting quality.—About 28 days on the plant about 6 days as a cut flower.

Fragrance: None.

Disease resistant:

*Botrytis.*—Resistant. As observed at Stuttgart.

Effect of weather: Very little.

Discoloration: Does not discolor after full bloom.

THE REPRODUCTIVE ORGANS

Stamens:

*Number.*—About 7.

*Arrangement.*—Around the ovaries.

*Anthers.*—Size: 1.5–2 mm. Color: Light Red.

*Filaments.*—Length: About 6–7 mm. Color: White.

*Pollen.*—Color: Golden Orange.

Pistils: Number: 1

*Styles.*—1. Length: About 6 mm.

*Stigmas.*—1. Color: Red.

Character of ovaries:

*Color.*—Pale green, length — about 4.5 mm. and pubescent.

Fruit:

*Fertility.*—The fruit is fertile.

*Shape.*—Ovoid.

*Color at maturity.*—Dark Brown.

This brilliant red geranium with dark green leaves blooms profusely over the bushy foliage body. The flower clusters are large and long lasting.

The distinction of the variety Klesec over the variety Isabell resides particularly in the plant type at the end of September where Klesec is 24 cm. and Isabell is about 30 cm. The flower colors of Klesec and Isabell are about the same, namely about 40-A. The color of the leaves, however, is quite different. For Klesec the leaf color is 147-A with a zone of 136-A whereas Isabell has a leaf color of 137-B with the center of the leaf 137-C. Also, the umbel size of Klesec is smaller than that for Isabell.

I claim:

1. The new and distinctive Geranium plant, substantially as herein shown and described, characterized by its green leaves and its contrasting and profusely blooming large brilliant red flower clusters.

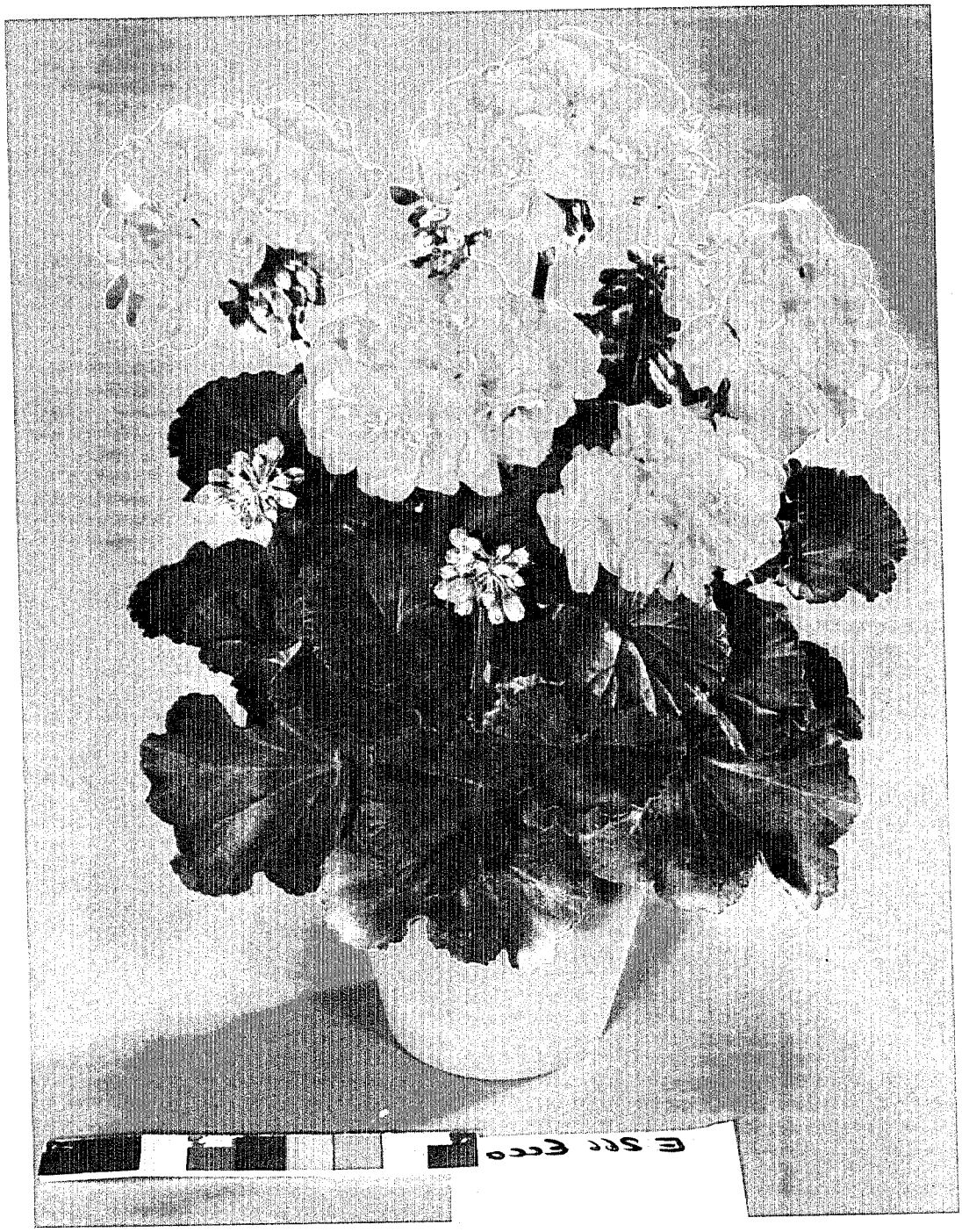

* * * * *